(12) United States Patent
Hunt

(10) Patent No.: US 11,076,800 B2
(45) Date of Patent: Aug. 3, 2021

(54) METHOD OF PROVIDING A PHYSIOTHERAPEUTIC PROTOCOL

(71) Applicant: Glynn C. Hunt, Spring Grove, PA (US)

(72) Inventor: Glynn C. Hunt, Spring Grove, PA (US)

(*) Notice: Subject to any disclaimer, the term of this patent is extended or adjusted under 35 U.S.C. 154(b) by 316 days.

(21) Appl. No.: 15/936,487

(22) Filed: Mar. 27, 2018

(65) Prior Publication Data

US 2019/0298256 A1 Oct. 3, 2019

(51) Int. Cl.
*A61B 5/00* (2006.01)
*G16H 50/20* (2018.01)
*G16H 20/30* (2018.01)

(52) U.S. Cl.
CPC .......... *A61B 5/4824* (2013.01); *A61B 5/4884* (2013.01); *A61B 5/746* (2013.01); *A61B 5/7465* (2013.01); *G16H 20/30* (2018.01); *G16H 50/20* (2018.01)

(58) Field of Classification Search
CPC .................................................... A61B 5/4824
USPC ........................................................ 434/247
See application file for complete search history.

(56) References Cited

U.S. PATENT DOCUMENTS

2016/0098090 A1* 4/2016 Klein .................... G06F 3/0482
345/156

* cited by examiner

*Primary Examiner* — Kesha Frisby

(57) ABSTRACT

A physiotherapeutic protocol is provided to a user having an injury and includes providing access to the user to download or install a predetermined computing application and registering their particulars. A treatment protocol is determined for the user in response to user selection of one or more predetermined injuries, the protocol includes a plurality of sessions of physiotherapeutic treatment exercises and techniques. The user provides predetermined information corresponding to functional levels of the user about their injury or damaged site and establishing one or more initial user functional levels and are guided through the treatment protocol exercises and techniques in a predetermined order to treat their injury. user input is received before and/or during and/or after each treatment session user functional levels and when for three successive user functional level entries I, II and III alerting the user and interrupting the protocol if functional levels I compared to II, and II compared to III exceed predetermined values, or if there is no improvement in functional level between functional levels I and II and levels II and III.

10 Claims, 31 Drawing Sheets

FIG.11

Lower Extremity Functional Scale (LEFS)

Source: Binkley JM, Stratford PW, Lott SA, Riddle DL. The Lower Extremity Functional Scale (LEFS): scale development, measurement properties, and clinical application. North American Orthopaedic Rehabilitation Research Network. *Phys Ther.* 1999 Apr;79(4):371-83.

The Lower Extremity Functional Scale (LEFS) is a questionnaire containing 20 questions about a person's ability to perform everyday tasks. The LEFS can be used by clinicians as a measure of patients' initial function, ongoing progress and outcome, as well as to set functional goals.

The LEFS can be used to evaluate the functional impairment of a patient with a disorder of one or both lower extremities. It can be used to monitor the patient over time and to evaluate the effectiveness of an intervention.

Scoring instructions

The columns on the scale are summed to get a total score. The maximum score is 80.

Interpretation of scores

- The lower the score the greater the disability.
- The minimal detectable change is 9 scale points.
- The minimal clinically important difference is 9 scale points.
- % of maximal function = (LEFS score) / 80 * 100

Performance:

- The potential error at a given point in time was +/- 5.3 scale points.
- Test-retest reliability was 0.94.
- Construct reliability was determined by comparison with the SF-36. The scale was found to be reliable with a sensitivity to change superior to the SF-36.

FIG.24.1

Lower Extremity Functional Scale (LEFS)

Instructions

We are interested in knowing whether you are having any difficulty at all with the activities listed below because of your lower limb problem for which you are currently seeking attention. Please provide an answer for each activity.

**Today, *do you* or *would you* have any difficulty at all with:**

| Activities | Extreme difficulty or unable to perform activity | Quite a bit of difficulty | Moderate difficulty | A little bit of difficulty | No difficulty |
|---|---|---|---|---|---|
| 1. Any of your usual work, housework or school activities. | 0 | 1 | 2 | 3 | 4 |
| 2. Your usual hobbies, recreational or sporting activities. | 0 | 1 | 2 | 3 | 4 |
| 3. Getting into or out of the bath. | 0 | 1 | 2 | 3 | 4 |
| 4. Walking between rooms. | 0 | 1 | 2 | 3 | 4 |
| 5. Putting on your shoes or socks. | 0 | 1 | 2 | 3 | 4 |
| 6. Squatting. | 0 | 1 | 2 | 3 | 4 |
| 7. Lifting an object, like a bag of groceries from the floor. | 0 | 1 | 2 | 3 | 4 |
| 8. Performing light activities around your home. | 0 | 1 | 2 | 3 | 4 |
| 9. Performing heavy activities around your home. | 0 | 1 | 2 | 3 | 4 |
| 10. Getting into or out of a car. | 0 | 1 | 2 | 3 | 4 |
| 11. Walking 2 blocks. | 0 | 1 | 2 | 3 | 4 |
| 12. Walking a mile. | 0 | 1 | 2 | 3 | 4 |
| 13. Going up or down 10 stairs (about 1 flight of stairs). | 0 | 1 | 2 | 3 | 4 |
| 14. Standing for 1 hour. | 0 | 1 | 2 | 3 | 4 |
| 15. Sitting for 1 hour. | 0 | 1 | 2 | 3 | 4 |
| 16. Running on even ground. | 0 | 1 | 2 | 3 | 4 |
| 17. Running on uneven ground. | 0 | 1 | 2 | 3 | 4 |
| 18. Making sharp turns while running fast. | 0 | 1 | 2 | 3 | 4 |
| 19. Hopping. | 0 | 1 | 2 | 3 | 4 |
| 20. Rolling over in bed. | 0 | 1 | 2 | 3 | 4 |
| Column Totals: | 0 | 1 | 2 | 3 | 4 |

FIG.24/2

Neck Disability Index

This questionnaire is designed to help us better understand how your neck pain affects your ability to manage everyday -life activities. Please mark in each section the one box that applies to you. Although you may consider that two of the statements in any one section relate to you, please mark the box that most closely describes your present -day situation.

Section 1 - Pain Intensity

- ☐ I have no pain at the moment.
- ☐ The pain is very mild at the moment.
- ☐ The pain is moderate at the moment.
- ☐ The pain is fairly severe at the moment.
- ☐ The pain is very severe at the moment.
- ☐ The pain is the worst imaginable at the moment.

Section 2 - Personal Care

- ☐ I can look after myself normally without causing extra pain.
- ☐ I can look after myself normally, but it causes extra pain.
- ☐ It is painful to look after myself, and I am slow and careful.
- ☐ I need some help but manage most of my personal care.
- ☐ I need help every day in most aspects of self-care.
- ☐ I do not get dressed. I wash with difficulty and stay in bed.

Section 3 - Lifting

- ☐ I can lift heavy weights without causing extra pain.
- ☐ I can lift heavy weights, but it gives me extra pain.
- ☐ Pain prevents me from lifting heavy weights off the floor but I can manage if items are conveniently positioned, ie. on a table.
- ☐ Pain prevents me from lifting heavy weights, but I can manage light weights if they are conveniently positioned.
- ☐ I can lift only very light weights.
- ☐ I cannot lift or carry anything at all.

Section 4 - Work

- ☐ I can do as much work as I want.
- ☐ I can only do my usual work, but no more.
- ☐ I can do most of my usual work, but no more.
- ☐ I can't do my usual work.
- ☐ I can hardly do any work at all.
- ☐ I can't do any work at all.

Section 5 - Headaches

- ☐ I have no headaches at all.
- ☐ I have slight headaches that come infrequently.
- ☐ I have moderate headaches that come infrequently.
- ☐ I have moderate headaches that come frequently.
- ☐ I have severe headaches that come frequently.
- ☐ I have headaches almost all the time.

Section 6 - Concentration

- ☐ I can concentrate fully without difficulty.
- ☐ I can concentrate fully with slight difficulty.
- ☐ I have a fair degree of difficulty concentrating.
- ☐ I have a lot of difficulty concentrating.
- ☐ I have a great deal of difficulty concentrating.
- ☐ I can't concentrate at all.

Section 7 - Sleeping

- ☐ I have no trouble sleeping.
- ☐ My sleep is slightly disturbed for less than 1 hour.
- ☐ My sleep is mildly disturbed for up to 1-2 hours.
- ☐ My sleep is moderately disturbed for up to 2-3 hours.
- ☐ My sleep is greatly disturbed for up to 3-5 hours.
- ☐ My sleep is completely disturbed for up to 5-7 hours.

Section 8 - Driving

- ☐ I can drive my car without neck pain.
- ☐ I can drive as long as I want with slight neck pain.
- ☐ I can drive as long as I want with moderate neck pain.
- ☐ I can't drive as long as I want because of moderate neck pain.
- ☐ I can hardly drive at all because of severe neck pain.
- ☐ I can't drive my care at all because of neck pain.

Section 9 - Reading

- ☐ I can read as much as I want with no neck pain.
- ☐ I can read as much as I want with slight neck pain.
- ☐ I can read as much as I want with moderate neck pain.
- ☐ I can't read as much as I want because of moderate neck pain.
- ☐ I can't read as much as I want because of severe neck pain.
- ☐ I can't read at all.

Section 10 - Recreation

- ☐ I have no neck pain during all recreational activities.
- ☐ I have some neck pain with all recreational activities.
- ☐ I have some neck pain with a few recreational activities.
- ☐ I have neck pain with most recreational activities.
- ☐ I can hardly do recreational activities due to neck pain.
- ☐ I can't do any recreational activities due to neck pain.

Patient Name _____   Date _____

Score _____ [50]                    Benchmark   -5 = _____

Copyright: Vernon H. and Hagino C., 1987. Vernon H, Mior S. The Neck Disability Index: A study of reliability and validity. Journal of Manipulative and Physiological Therapeutics 1991; 14:409-415. Copied with permission of the authors.

FIG. 25/1

Oswestry Disability Questionnaire

This questionnaire has been designed to give us information as to how your back or leg pain is affecting your ability to manage in everyday life. Please answer by checking one box in each section for the statement which best applies to you. We realise you may consider that two or more statements in any one section apply but please just shade out the spot that indicates the statement which most clearly describes your problem.

Section 1: Pain Intensity

☐ I have no pain at the moment
☐ The pain is very mild at the moment
☐ The pain is moderate at the moment
☐ The pain is fairly severe at the moment
☐ The pain is very severe at the moment
☐ The pain is the worst imaginable at the moment

Section 2: Personal Care (eg. washing, dressing)

☐ I can look after myself normally without causing extra pain
☐ I can look after myself normally but it causes extra pain
☐ It is painful to look after myself and I am slow and careful
☐ I need some help but can manage most of my personal care
☐ I need help every day in most aspects of self-care
☐ I do not get dressed, wash with difficulty and stay in bed

Section 3: Lifting

☐ I can lift heavy weights without extra pain
☐ I can lift heavy weights but it gives me extra pain
☐ Pain prevents me lifting heavy weights off the floor but I can manage if they are conveniently placed eg. on a table
☐ Pain prevents me lifting heavy weights but I can manage light to medium weights if they are conveniently positioned
☐ I can only lift very light weights
☐ I cannot lift or carry anything

Section 4: Walking*

☐ Pain does not prevent me walking any distance
☐ Pain prevents me from walking more than 2 kilometres
☐ Pain prevents me from walking more than 1 kilometre
☐ Pain prevents me from walking more than 500 metres
☐ I can only walk using a stick or crutches
☐ I am in bed most of the time

Section 5: Sitting

☐ I can sit in any chair as long as I like
☐ I can only sit in my favourite chair as long as I like
☐ Pain prevents me sitting more than one hour
☐ Pain prevents me from sitting more than 30 minutes
☐ Pain prevents me from sitting more than 10 minutes
☐ Pain prevents me from sitting at all

Section 6: Standing

☐ I can stand as long as I want without extra pain
☐ I can stand as long as I want but it gives me extra pain
☐ Pain prevents me from standing for more than 1 hour
☐ Pain prevents me from standing for more than 30 minutes
☐ Pain prevents me from standing for more than 10 minutes
☐ Pain prevents me from standing at all

Section 7: Sleeping

☐ My sleep is never disturbed by pain
☐ My sleep is occasionally disturbed by pain
☐ Because of pain I have less than 6 hours sleep
☐ Because of pain I have less than 4 hours sleep
☐ Because of pain I have less than 2 hours sleep
☐ Pain prevents me from sleeping at all

Section 8: Sex Life (if applicable)

☐ My sex life is normal and causes no extra pain
☐ My sex life is normal but causes some extra pain
☐ My sex life is nearly normal but is very painful
☐ My sex life is severely restricted by pain
☐ My sex life is nearly absent because of pain
☐ Pain prevents any sex life at all

Section 9: Social Life

☐ My social life is normal and gives me no extra pain
☐ My social life is normal but increases the degree of pain
☐ Pain has no significant effect on my social life apart from limiting my more energetic interests e.g. sport
☐ Pain has restricted my social life and I do not go out as often
☐ Pain has restricted my social life to my home
☐ I have no social life because of pain

Section 10: Travelling

☐ I can travel anywhere without pain
☐ I can travel anywhere but it gives me extra pain
☐ Pain is bad but I manage journeys over two hours
☐ Pain restricts me to journeys of less than one hour
☐ Pain restricts me to short necessary journeys under 30 minutes
☐ Pain prevents me from travelling except to receive treatment

FIG.25/2

Score: /  x 100 =    %

Scoring: For each section the total possible score is 5: if the first statement is marked the section score = 0, if the last statement is marked it = 5. If all ten sections are completed the score is calculated as follows:
Example:  16 (total scored)
50 (total possible score) x 100 = 32%

If one section is missed or not applicable the score is calculated:   16 (total scored)
45 (total possible score) x 100 = 35.5%

Minimum Detectable Change (90% confidence): 10%points (Change of less than this may be attributable to error in the measurement)

Source:  Fairbank JCT & Pynsent, PB (2000) The Oswestry Disability Index. *Spine*, 25(22):2940-2953.
Davidson M & Keating J (2001) A comparison of five low back disability questionnaires: reliability and responsiveness. Physical Therapy 2002;82:8-24.

*Note: Distances of 1mile, ½ mile and 100 yards have been replaced by metric distances in the Walking section.

FIG.25/3

QuickDASH

Please rate your ability to do the following activities in the last week by circling the number below the appropriate response.

| | NO DIFFICULTY | MILD DIFFICULTY | MODERATE DIFFICULTY | SEVERE DIFFICULTY | UNABLE |
|---|---|---|---|---|---|
| 1. Open a tight or new jar. | 1 | 2 | 3 | 4 | 5 |
| 2. Do heavy household chores (e.g., wash walls, floors). | 1 | 2 | 3 | 4 | 5 |
| 3. Carry a shopping bag or briefcase. | 1 | 2 | 3 | 4 | 5 |
| 4. Wash your back. | 1 | 2 | 3 | 4 | 5 |
| 5. Use a knife to cut food. | 1 | 2 | 3 | 4 | 5 |
| 6. Recreational activities in which you take some force or impact through your arm, shoulder or hand (e.g., golf, hammering, tennis, etc.). | 1 | 2 | 3 | 4 | 5 |

| | NOT AT ALL | SLIGHTLY | MODERATELY | QUITE A BIT | EXTREMELY |
|---|---|---|---|---|---|
| 7. During the past week, to what extent has your arm, shoulder or hand problem interfered with your normal social activities with family, friends, neighbours or groups? | 1 | 2 | 3 | 4 | 5 |

| | NOT LIMITED AT ALL | SLIGHTLY LIMITED | MODERATELY LIMITED | VERY LIMITED | UNABLE |
|---|---|---|---|---|---|
| 8. During the past week, were you limited in your work or other regular daily activities as a result of your arm, shoulder or hand problem? | 1 | 2 | 3 | 4 | 5 |

Please rate the severity of the following symptoms in the last week. (circle number)

| | NONE | MILD | MODERATE | SEVERE | EXTREME |
|---|---|---|---|---|---|
| 9. Arm, shoulder or hand pain. | 1 | 2 | 3 | 4 | 5 |
| 10. Tingling (pins and needles) in your arm, shoulder or hand. | 1 | 2 | 3 | 4 | 5 |

| | NO DIFFICULTY | MILD DIFFICULTY | MODERATE DIFFICULTY | SEVERE DIFFICULTY | SO MUCH DIFFICULTY THAT I CAN'T SLEEP |
|---|---|---|---|---|---|
| 11. During the past week, how much difficulty have you had sleeping because of the pain in your arm, shoulder or hand? (circle number) | 1 | 2 | 3 | 4 | 5 |

QuickDASH DISABILITY/SYMPTOM SCORE = $\left(\left[\frac{\text{sum of n responses}}{n}\right] - 1\right) 25$, where n is equal to the number of completed responses.

A QuickDASH score may not be calculated if there is greater than 1 missing item.

FIG.26

METHOD OF PROVIDING A PHYSIOTHERAPEUTIC PROTOCOL

CROSS REFERENCE TO RELATED APPLICATIONS

This applications claims priority under the Paris Convention from Australian Patent Application Number 2017901084 filed 27 Mar. 2017 and New Zealand Patent Application Number 730530 filed 27 Mar. 2017.

FIELD OF THE INVENTION

The present invention relates to physiotherapeutic treatments of injuries to a user, and in particular, a physiotherapeutic protocol as an alternative to formal physiotherapeutic medical practitioner treatment.

The invention has been developed primarily with respect to physiotherapeutic injuries that typically require direct physiotherapy practitioner consultation and will be described hereinafter with reference to this application. However, it will be appreciated the invention is not limited to this particular field of use.

BACKGROUND OF THE INVENTION

It has been long known to provide exercise protocols or guides and programs to users in need thereof. These have been available via books and recently by the internet. In the exercise market particularly, this has also been extended to allow people to record details of their exercise to allow progress to be plotted, usually with some goal in mind.

When a person sustains an injury that requires physiotherapy-type treatment to improve or restore the injured region they may or may not need to visit a physiotherapeutic medical practitioner. This is particularly the case for post-surgery or interventional treatment to an injury. A user may, for example, feel they do not require to expend the sometimes significant funds and to commit the necessary time associated with visiting a physiotherapeutic practitioner. Further, if they feel their injury is not particularly extensive, they may look up exercises or groups of exercises specifically known for assisting in treating a particular injury.

For example, exercises for the recovery of a specific muscle tear, ligament damage or bone fracture amongst many other injuries have well known exercise or rehabilitation protocols that can be employed. Historically these were in pamphlet form and are now in digital form, especially available via the internet. Commonly, specific software is provided for physiotherapeutic practitioners including via tablet and smartphone application software that is used by the practitioner to plan treatment and to record and track progress of the treatment of a patient.

An example of such modern software is readily available via smartphone or computer software suppliers and may be general or specific to particular parts of the body, for example lower limbs. Such software is configured toward the clinically relevant injuries for physiotherapeutic and other health care professionals to record and view the information but to also present to their clients. Reference tools such as known rehabilitation protocol programs, for example are provided and typically a practitioner is able to select an injury from a predetermined list thereof. Exercises that can be used to form a treatment protocol for the patient are then selected by the practitioner in the software and the program is commenced with the patient. However, this necessarily requires on-going medical practitioner intervention.

Unfortunately, the known application software is directed toward practicing physiotherapists and other healthcare practitioners rather than the patient. For example, many such application software programs allow the medical practitioner to automatically generate relevant documents for use by other practitioners, such as in referrals. Whilst such application software is useful for a physiotherapy practitioner or other healthcare professional, a user having an injury or requiring rehabilitation necessarily needs to use such a professional and their associated costs otherwise they can risk not repairing the injury or exacerbating it.

GENESIS OF THE INVENTION

The genesis of the invention is a desire to provide a physiotherapeutic treatment protocol to a user to avoid the expense of engaging a physiotherapist or other medical practitioner where potential or undesirable outcomes of the users use of the protocol is alerted to the user, or to provide a useful alternative.

SUMMARY OF THE INVENTION

In accordance with a first aspect of the present invention there is disclosed a method of providing a physiotherapeutic protocol to a user having an injury, the method comprising the steps of:
  providing access to the user to download or install a predetermined computing application;
  registering the particulars of the user of the installed computing application;
  determining a treatment protocol for the user in response to user selection of one or more predetermined injuries, the protocol including a plurality of sessions of physiotherapeutic treatment exercises and techniques;
  receiving predetermined information from the user corresponding to functional levels of the user about their injury or damaged site and establishing one or more initial user functional levels;
  guiding the user through the treatment protocol exercises and techniques in a predetermined order;
  receiving before and/or during and/or after each treatment session user functional levels;
  wherein for three successive user functional level entries I, II and III alerting the user and interrupting the protocol if functional levels I compared to II, and II compared to III exceed predetermined values, or if there is no improvement in functional level between functional levels I and II and levels II and III.

According to a second aspect of the present invention there is provided a method of providing a physiotherapeutic protocol to a user having an injury, the method comprising the steps of:
  providing access to the user to download or install predetermined computing application;
  registering the particulars of the user of the installed computing application;
  determining a treatment protocol for the user in response to user selection of one or more predetermined injuries, the protocol including a plurality of sessions of physiotherapeutic treatment exercises and techniques;
  receiving predetermined information from the user corresponding to pain levels experienced by the user about their injury or damaged site and establishing one or more initial user pain levels;

guiding the user through the treatment protocol exercises and techniques in a predetermined order;

receiving before and/or during and/or after each treatment session user pain levels wherein for three successive user pain level entries I, II and III alerting the user and interrupting the protocol if pain levels I compared to II, and II compared to III exceed predetermined values, or if there is no improvement in pain level between functional levels I and II and levels II and III.

According to a third aspect of the present invention there is provided a method of providing a physiotherapeutic protocol to a user having an injury, the method comprising the steps of:

providing access to the user to download or install a predetermined computing application;

registering the particulars of the user of the installed computing application;

determining a treatment protocol for the user in response to user selection of one or more predetermined injuries, the protocol including a plurality of sessions of physiotherapeutic treatment exercises and techniques;

receiving predetermined information from the user corresponding to functional levels of the user about their injury or damaged site and establishing one or more initial user functional levels;

guiding the user through the treatment protocol exercises and techniques in a predetermined order;

receiving before and/or during and/or after each treatment session user functional levels;

wherein for successive user functional level entries I, II and III alerting the user and interrupting the protocol if functional level entry II is reduced by a predetermined amount compared to entry I, or if functional level entry III is reduced by a predetermined amount compared to entry II.

According to another aspect of the present invention there is provided a method of providing a physiotherapeutic protocol to a user having an injury, the method comprising the steps of:

providing access to the user to download or install predetermined computing application;

registering the particulars of the user of the installed computing application;

determining a treatment protocol for the user in response to user selection of one or more predetermined injuries, the protocol including a plurality of sessions of physiotherapeutic treatment exercises and techniques;

receiving predetermined information from the user corresponding to pain levels experienced by the user about their injury or damaged site and establishing one or more initial user pain levels;

guiding the user through the treatment protocol exercises and techniques in a predetermined order;

alerting the user if level II is greater than or equal to level I plus a factor of 3; or if level III is greater than or equal to level II plus a factor of 3.

It can be seen there is advantageously provided an alternative to formal rehabilitation care where a user is importantly alerted that they may need to seek medical practitioner care to prevent additional injury or worsening their condition. For example, a user may commence a physiotherapeutic treatment protocol and they would be alerted that it is either not providing the desired outcomes or that they had or are at further risk of exacerbating their injury, each ease being referred to consult a medical practitioner. This can prevent significant expense where a practitioner is not required but advantageously prevents exacerbation if one is not consulted.

BRIEF DESCRIPTION OF THE DRAWINGS

A preferred embodiment of the invention will now be described, by way of example only, with reference to the accompanying drawings in which:

FIG. 11 indicates user input of payment information for use for treatment protocol;

FIG. 24 is an example of a functional level of a user of their injury;

FIG. 25 is similar to FIG. 24 for a different region of the body;

FIG. 26 is similar to FIG. 24 but for a different region of the body;

DETAILED DESCRIPTION OF THE PREFERRED EMBODIMENTS

The preferred embodiment of the invention is described with respect to an implementation on a generic smartphone 1. However, it will be appreciated that smartphone 1 could be substituted for any preferred device configured to be able to run software applications either locally or via the internet (e.g., thin-client) or a hardware device or module such as an application specific integrated circuit including field programmable gate-arrays.

Figure 1:
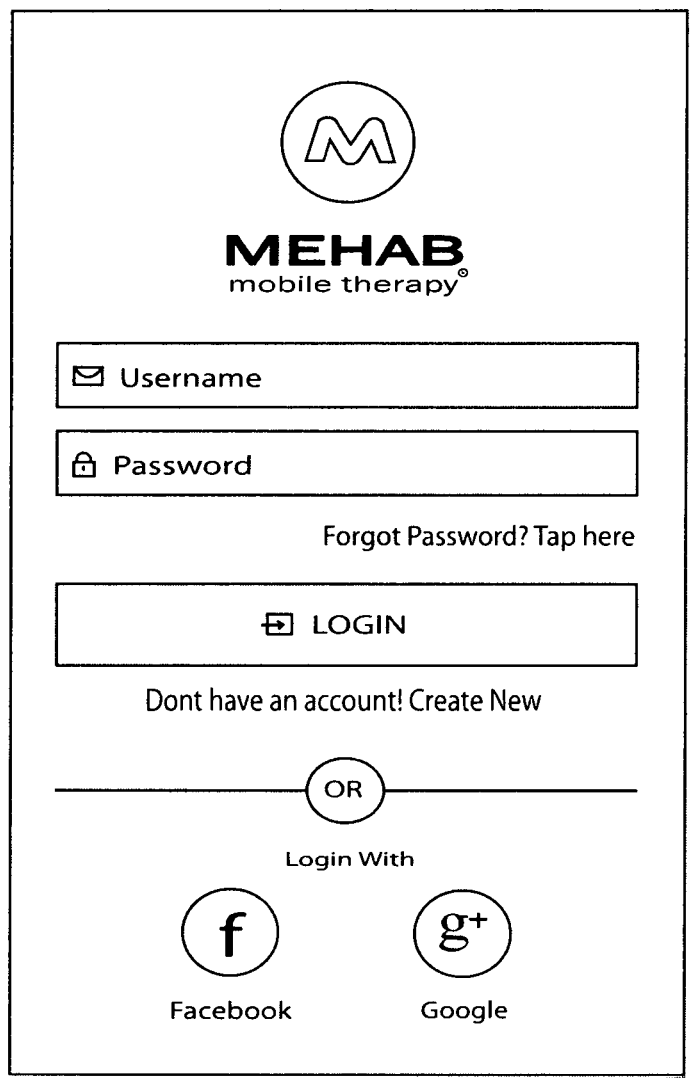
FIG. 1 is a schematic view of a smartphone operating a physiotherapy treatment protocol according to the preferred embodiment of the invention.

The preferred embodiment provides a method of operating a physiotherapeutic protocol to a user having an injury requiring rehabilitation. In such protocols, physical medicine is employed to assist healing or rehabilitation of an injury. Such injury may be acquired through sporting activity, or during surgery requiring physiotherapeutic wound care amongst a host of other reasons. In use, a user having an injury can download application software on their smartphone 1. An example is shown in FIG. 1 of a screenshot of the smartphone 1 for a registered user to login or for a new user to register to use the system.

Figure 2:
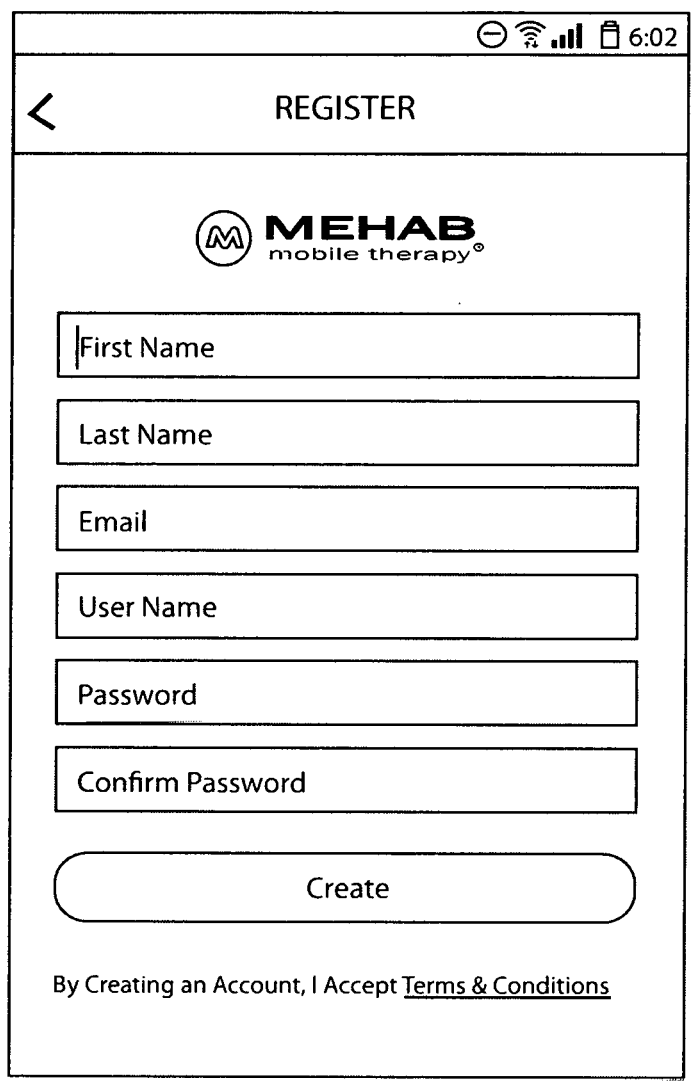
FIG. 2 shows a screenshot of the creation of an account for receiving a physiotherapy treatment protocol.
Figure 3:
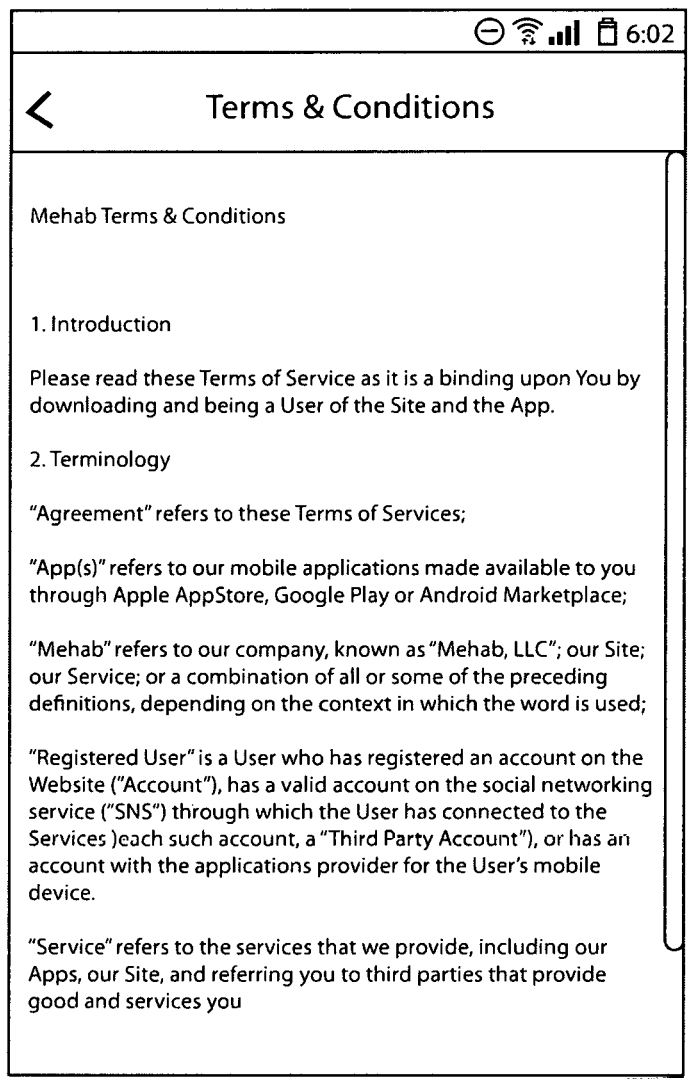
FIG. 3 is a schematic screenshot setting out e s and conditions of use of the physiotherapy treatment protocol.

FIG. 2 shows an example of at least part of a registration screen for a user. Conventional details including personal information and selection of a user name and password. A user can view the terms and conditions provided by a supplier of software for operating the physiotherapeutic protocol and this is shown with filler text in FIG. 3.

Figure 4:
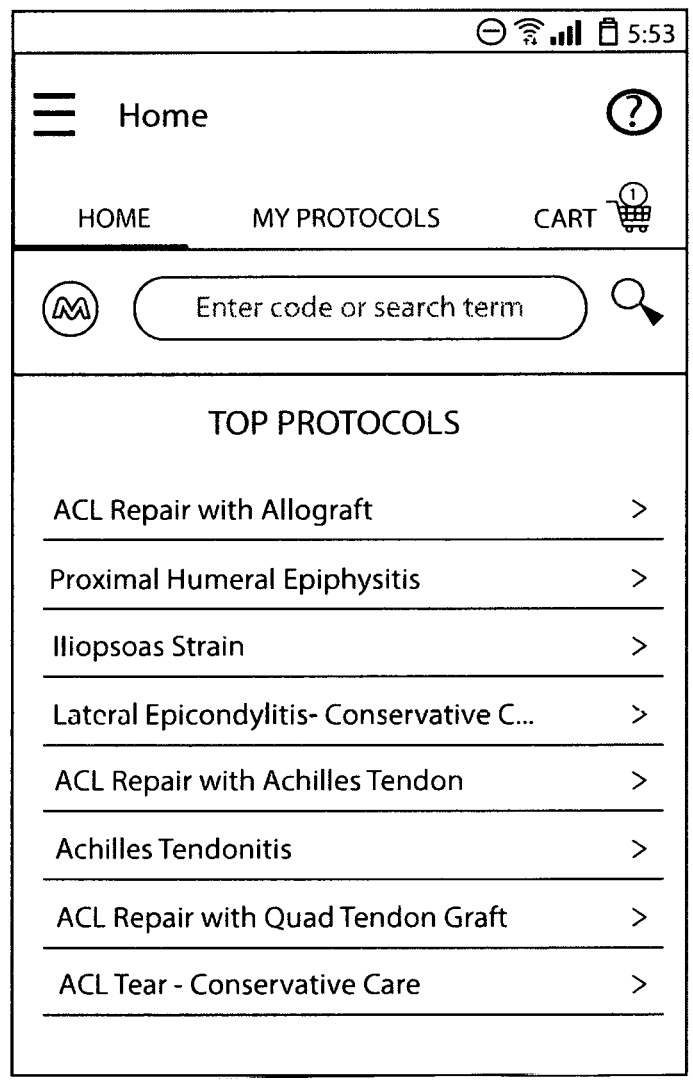
FIG. 4 is a subsequent screen of FIG. 1 allowing the user to select one or more predetermined injuries.

The user with an injury then selects from a predetermined list of injuries that could require rehabilitation one or more matching their injury/s. FIG. 3A provides a predetermined list of physiotherapeutic protocols that a user may select from. This is shown in FIG. 4 where the protocol is tailored to the injury of the user as dependent on their injury.

Figure 5:
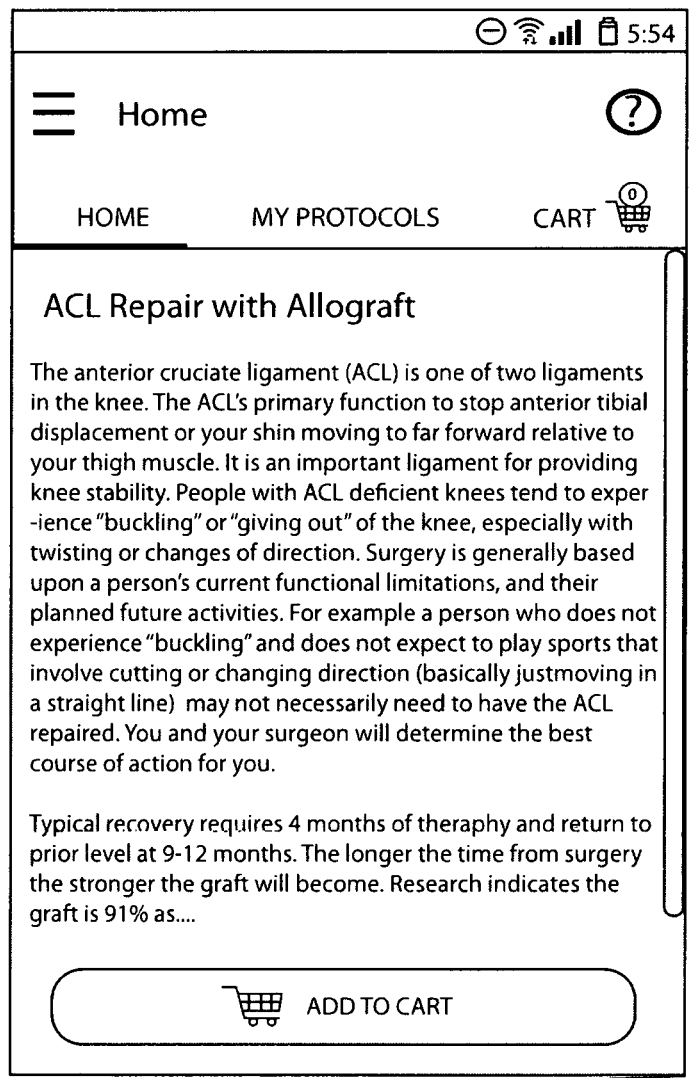
FIG. 5 is a schematic screenshot of information concerning a treatment protocol for a meniscal tear (selected by the user)

In the preferred embodiment, a meniscal tear is the injury selected by the user. Furthermore, a conservative level of treatment or care as understood by an appropriate medical practitioner is provided with that. Further, it will be seen in FIG. 4 that the user can acquire more than one protocol and these can be viewed under the tab "My Protocols". A checkout cart is also provided for when the injury/s are entered for the appropriate protocols. FIG. 5 is an indicative screenshot with filler text (Lorum Ipsum) for illustrative purposes. The information presented relates to the particulars of the meniscal tear injury selected in the preferred embodiment.

Figure 6:
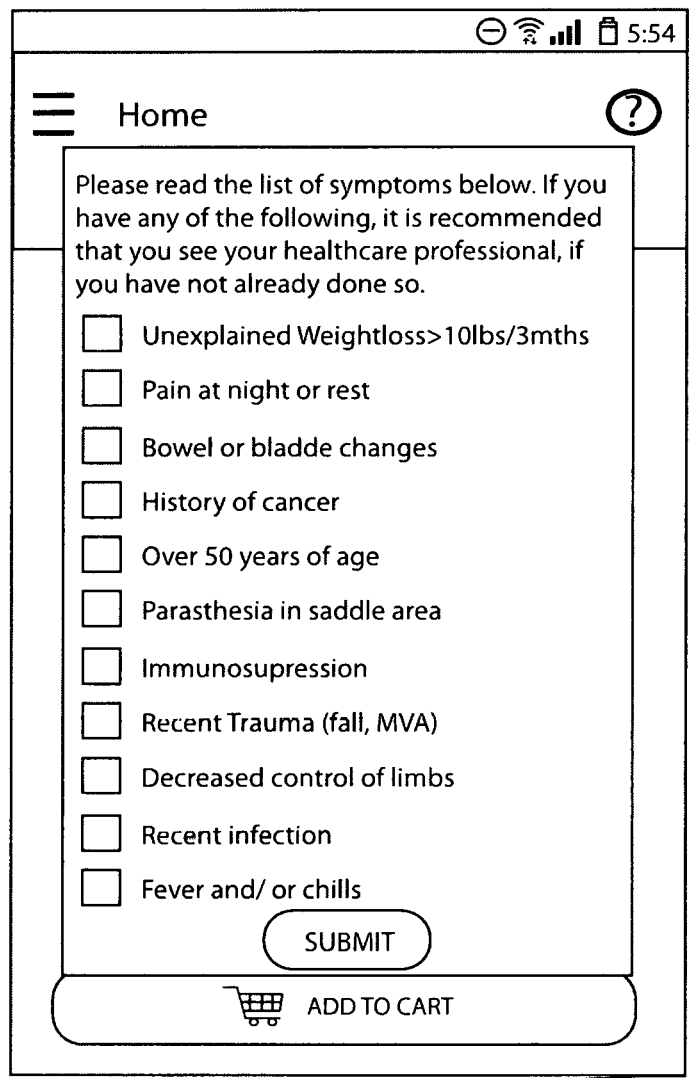
FIG. 6 is a subsequent screenshot receiving input from the user concerning indications that may prevent treatment.

Having selected the protocol to match their injury/s, as shown in FIG. 6, the user is presented with a list of conditions that may be particularly undesirable for a user to possess if they are to continue with a physiotherapeutic protocol/s they have selected to rehabilitate their injury. The checklist aims to identify well known symptoms of potentially major illness such as cancer or cardiac issues, for example.

Figure 7:
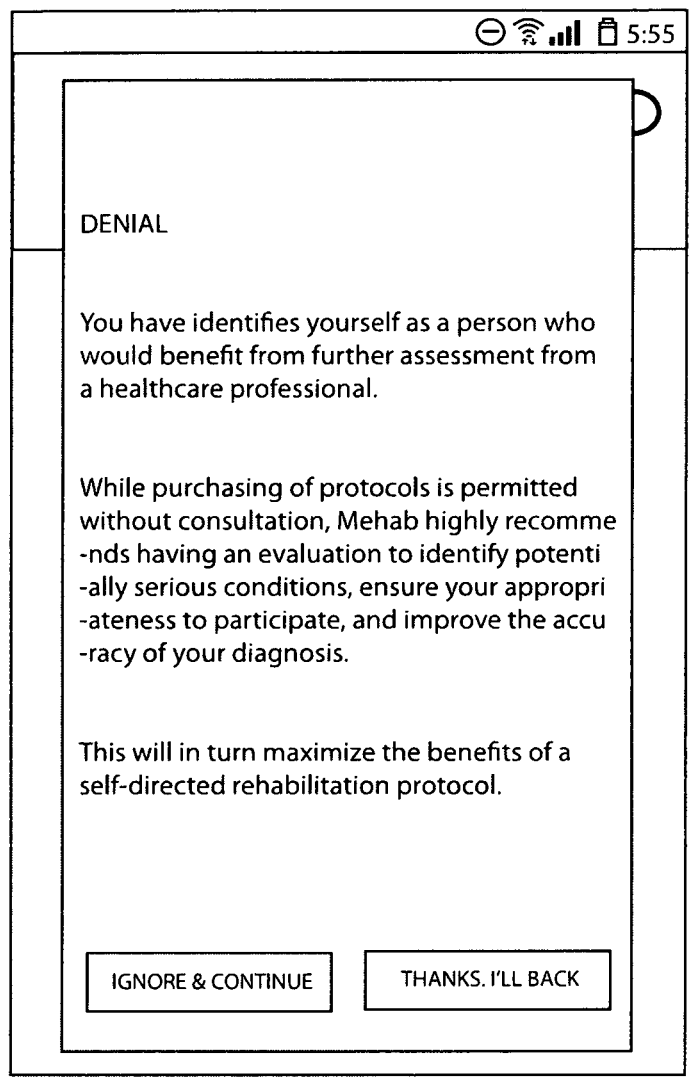
FIG. 7 is a subsequent screenshot to FIG. 6 providing a warning to a user.
Figure 8:
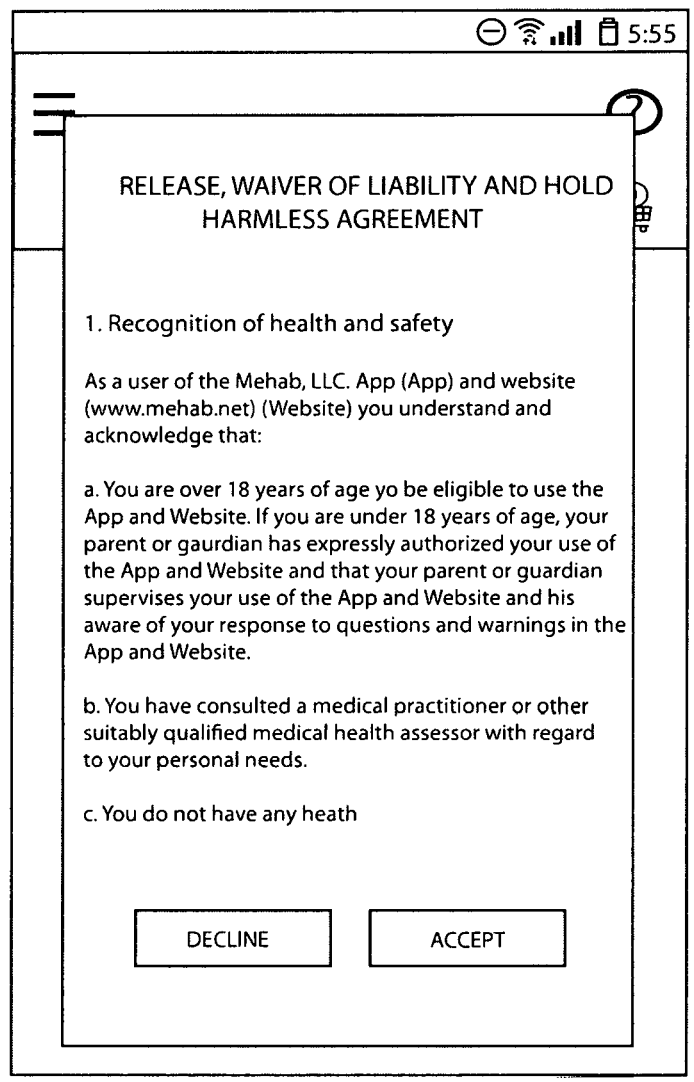
FIG. 8 is a disclaimer screen subsequent to the screen selection of FIG. 7.

FIG. 7 is a representation of a preferred response should the user be suffering from any of those selected conditions. In the preferred embodiment this includes advising the user that before proceeding they should see a registered medical professional such as a general practitioner to address any one or more of those potentially significant symptoms identified. The user also has the option to ignore this if they have seen a health care professional or if they otherwise choose to do so. Should the user select to either ignore the advice or if they have seen a health care professional accordingly, they are presented with a disclaimer or similar confirming the user has seen a health care professional or that they willfully choose not to. Again, filler text is used for illustrative purposes.

Figure 9:
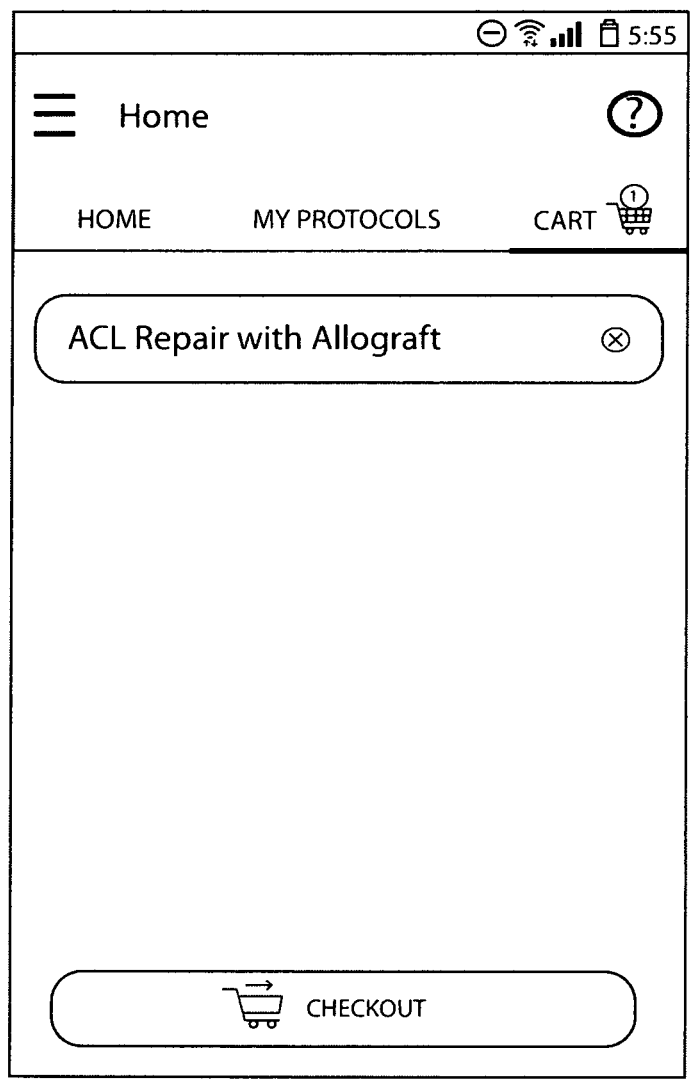
FIG. 9 confirms selection of user injury.
Figure 10:
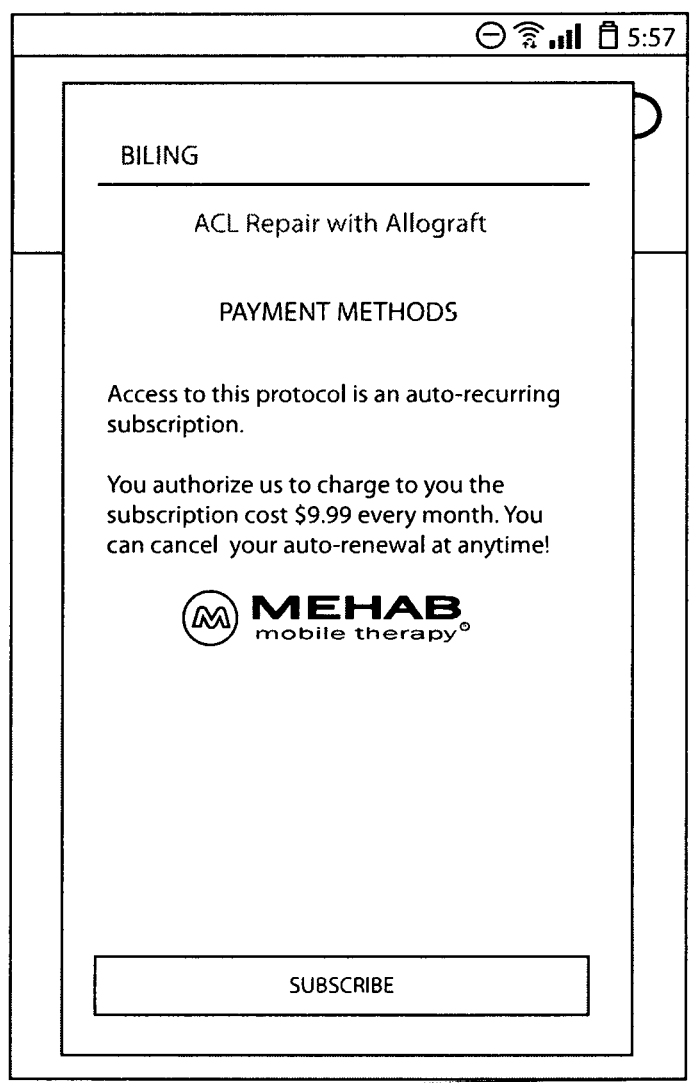
FIG. 10 presents a payment interface for the user to carry out the treatment protocol previously selected.

FIG. 9 is a schematic screenshot of the smartphone 1 where the user has selected the meniscal tear—conservative care and are able to proceed to acquire the meniscal tear protocol for use in treatment of their injury. The user then concludes the transaction by clicking or actuating the checkout tab and payment method for continuing are provided. The user then subscribes to the protocol for a predetermined time period, being monthly in the preferred embodiment of FIG. 10.

Figure 11:
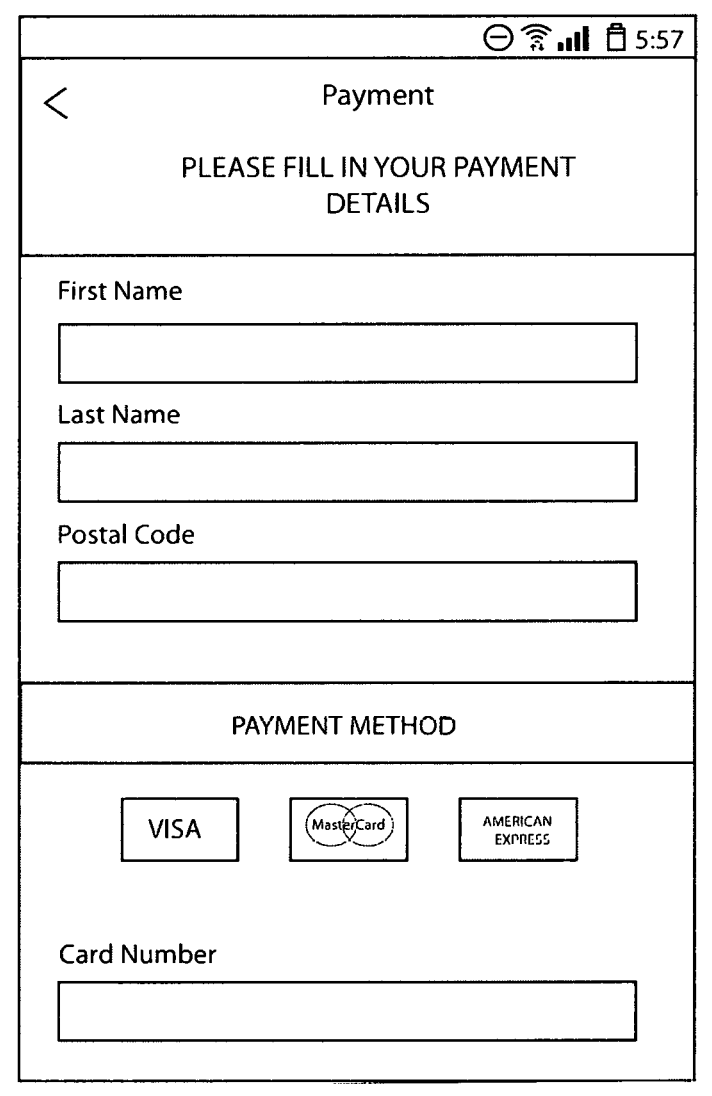

In other preferred embodiments of the invention, not illustrated, the user payment may be notionally zero or they may purchase the physiotherapeutic protocol in a single payment. Further, if the protocol is interact based in that the user interfaces via a web browser or the like including application virtualization such as a thin-client server, then user payment may be for access to use the protocol online. FIG. 11 shows an indicative screenshot obtaining user payment details by way of a credit card, for example, from a user. Any preferred payment method could of course be employed.

Once the physiotherapeutic protocol has been purchased by the user, it is active in the preferred embodiment for the monthly period which the user has subscribed. In the preferred embodiment shown in FIG. 12, the user selects their protocol/s being only the meniscal tear in the present case but it will be appreciated it could be others. Reporting data as described below is able to be observed by the user and an indication of the status of the protocol, namely active and available for use by the user is also displayed together with a period of time left.

Figure 12:
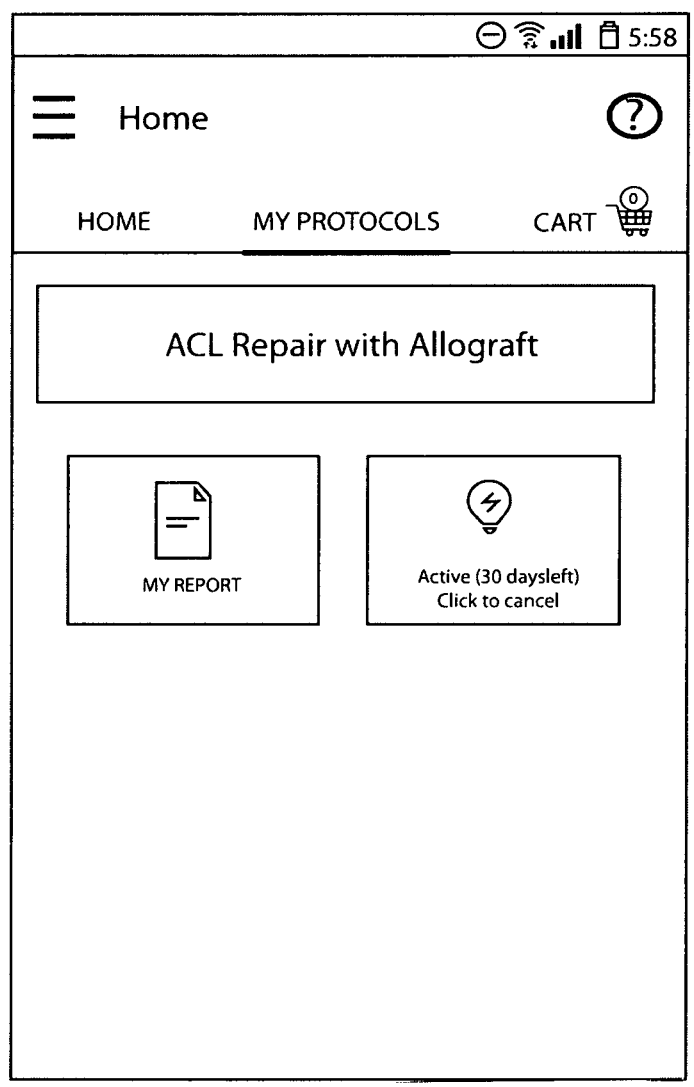
FIG. 12 is a summary of the treatment protocol purchased by the user.
Figure 13:
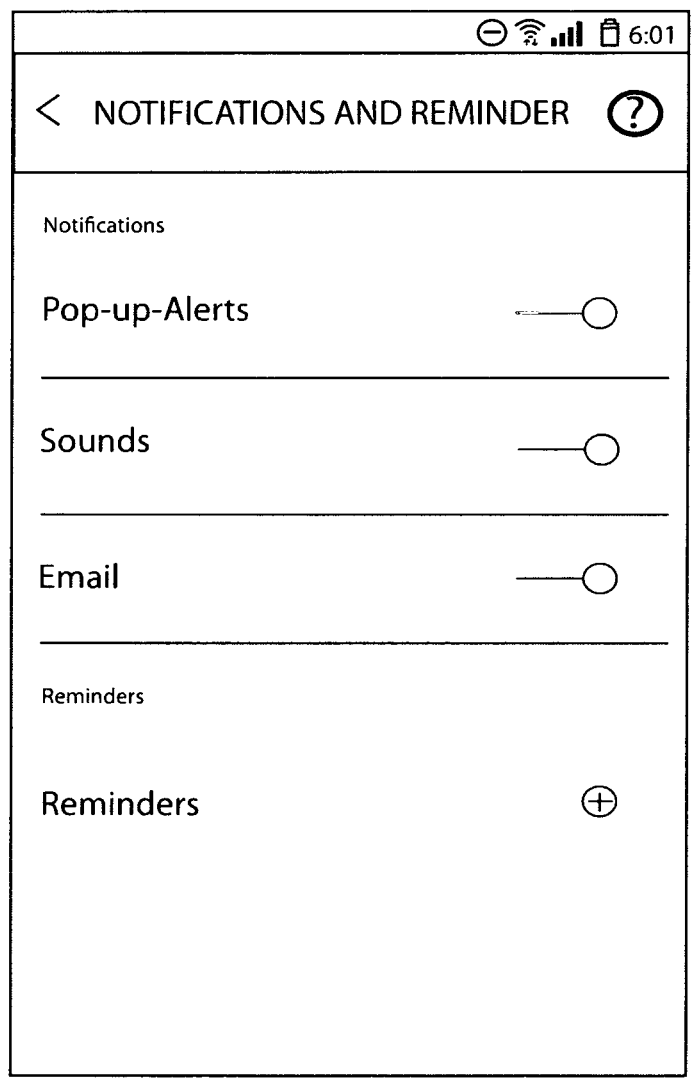
FIG. 13 shows notification types and reminders for conducting a protocol.

In the embodiment of FIG. 12, this is shown to be twenty three days remaining from a one month subscription. FIG. 13 shows options available for the user when carrying out the protocol. These include on-screen or email notifications, together with the option to have reminders to ensure user compliance with the selected protocol.

Figure 14:
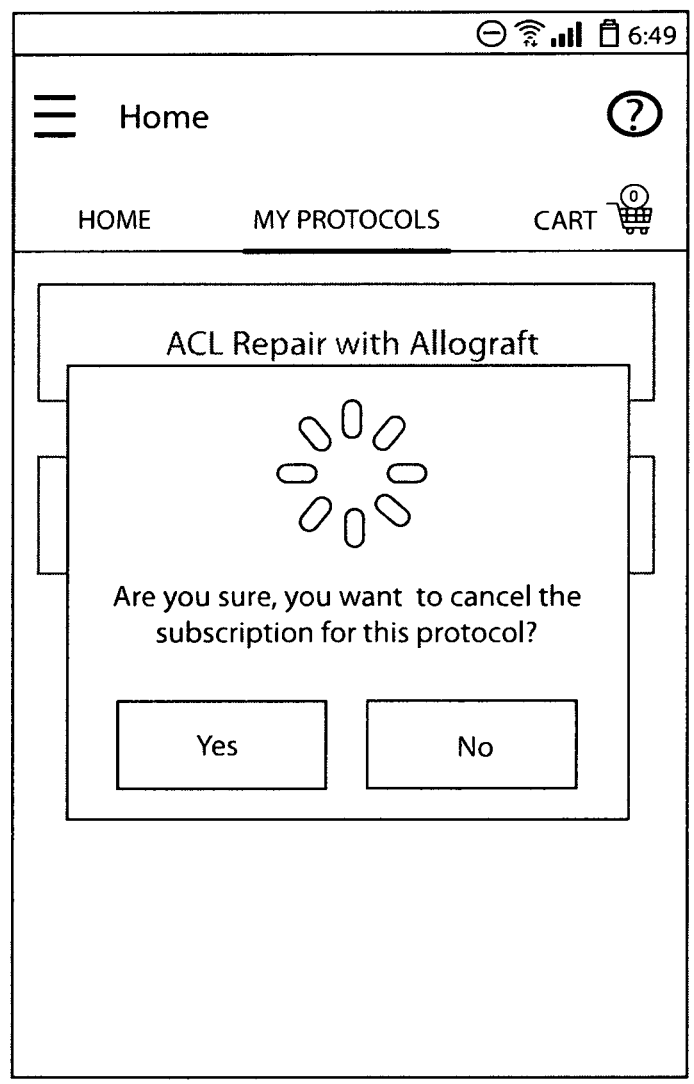
FIG. 14 shows an option for a user to cancel their subscription to user protocol or to reactivate same if suspended.
Figure 15:
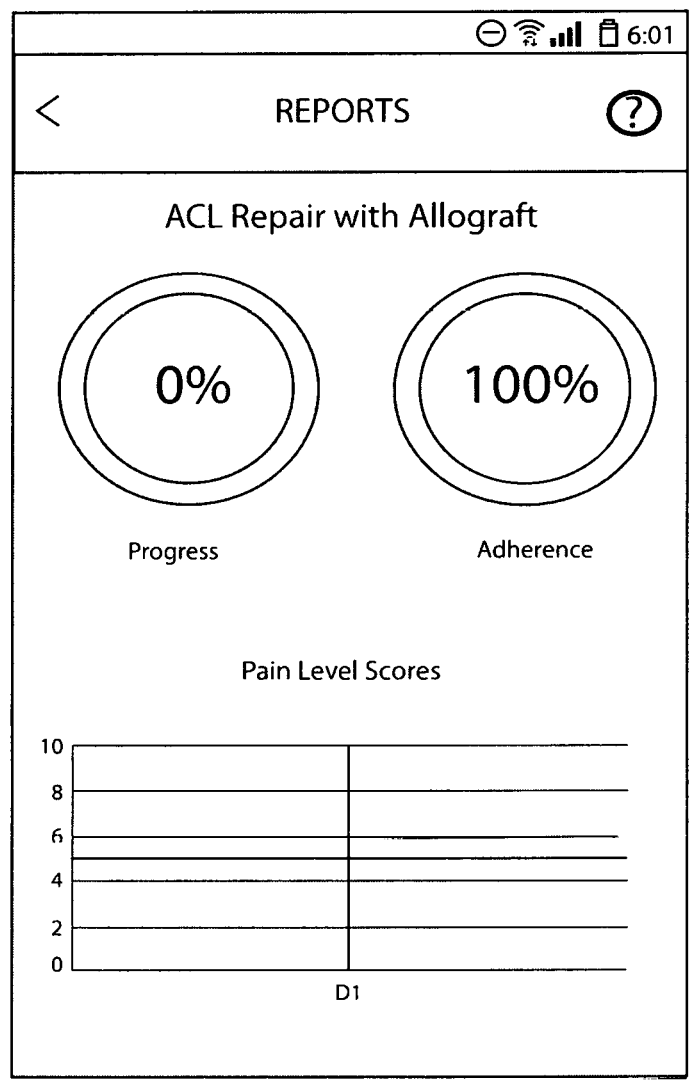
FIG. 15 is an example of a progress report of the selected injury over time for the user.

FIG. 14 is an indicative screenshot of an option available to the user to cancel their subscription or if it has been deactivated, to reactivate it. This may be appropriate in circumstances where some event requires interruption of the user carrying out the protocol. FIG. 15 shows an example of a screen provided to the user when they select "My Report" option shown in FIG. 12. In the preferred embodiment, various parameters are indicated including the progression percentage through the total protocol for the meniscal tear. This is shown as 63% of the protocol completed (see FIG. 16) in the preferred embodiment.

An adherence indicator is also provided and this indicates whether the user has been using the protocol during expected time periods and whether any aspects of the protocol have been missed. Also indicated are graphical measures over time of functional measures made by the user during progression of the protocol. Pain level indications are also shown in the bottom graph of FIG. 15, however, zero pain levels are entered in the preferred embodiment shown.

Figure 16:
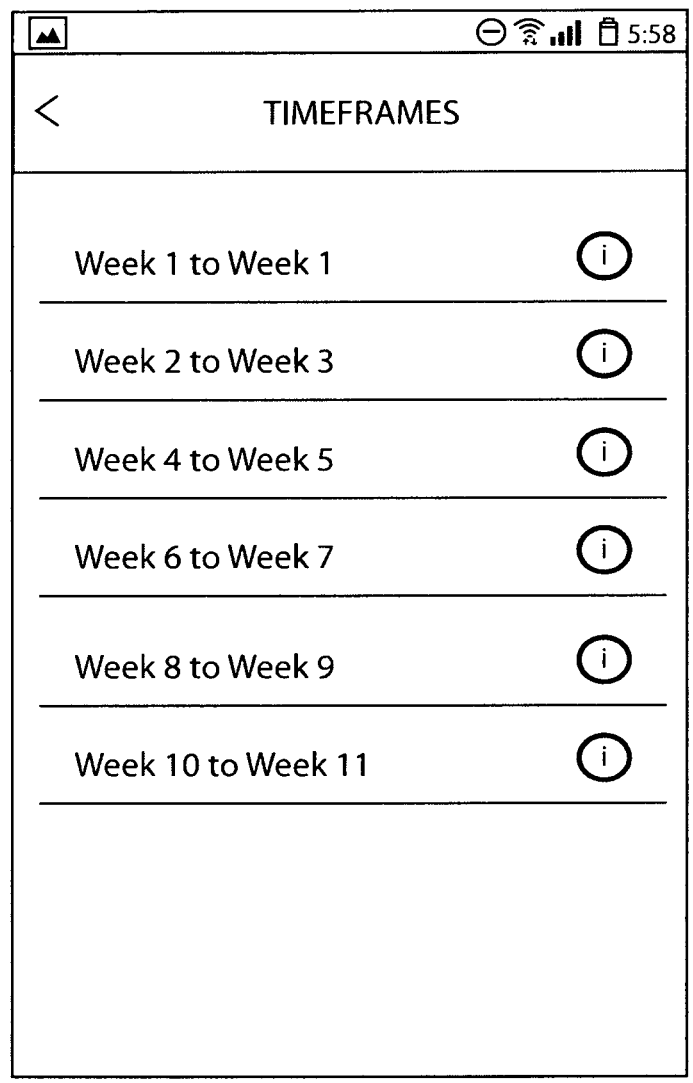
FIG. 16 shows predetermined timeframes for the user for the selected injury.

FIG. 16 shows an indicative screenshot of timetables for operation of the protocol for the display of a user. In the meniscal tear protocol, these are divided up into six two week blocks and information can be obtained for each aspect of the protocol in operation during those weeks. A post-operative period of six days is also indicated for the protocol for the meniscal tear.

Figure 17:
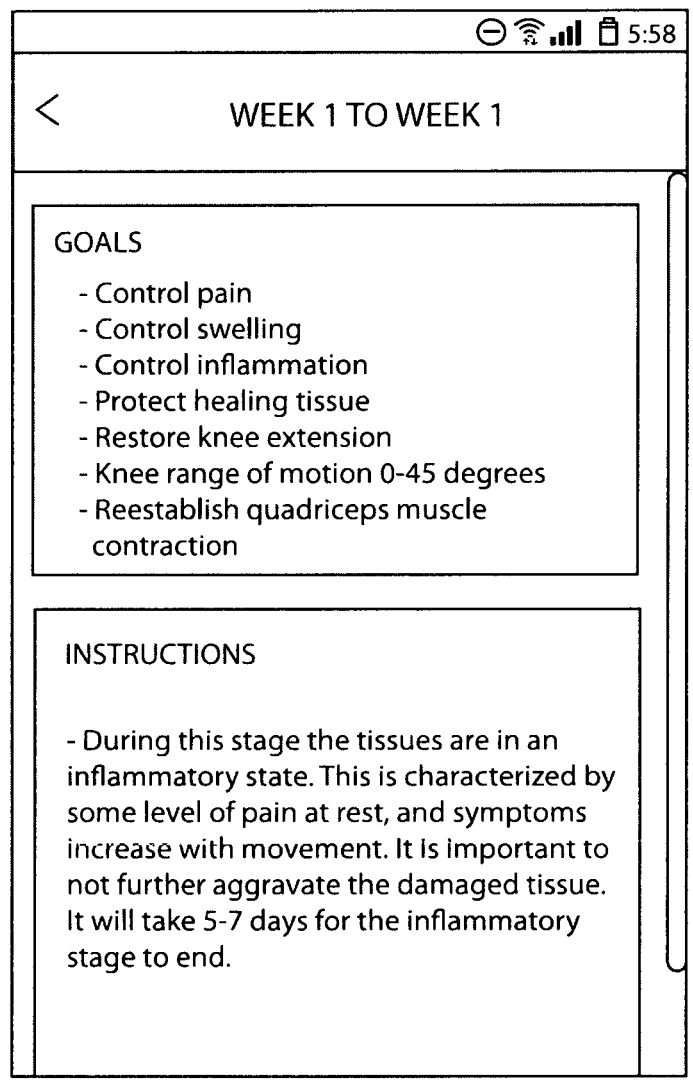
FIG. 17 is intended to provide specific treatment protocol, precautions and instructions.

FIG. 17 is an example of a screenshot of the postoperative days 1-6 timeframe when a user actuates the symbol letter 'I' surrounded by a circle in the screenshot if FIG. 16. In the example, the goals for that time frame are set out together with any appropriate cautions to be provided to a user so as to either conduct the protocol in a proper manner or to avoid further injury or exacerbation of the meniscal tear. Instructions for carrying out the protocol are then provided. Again, Lorem Ipsum filler text is shown for illustrative purposes.

Figure 18:
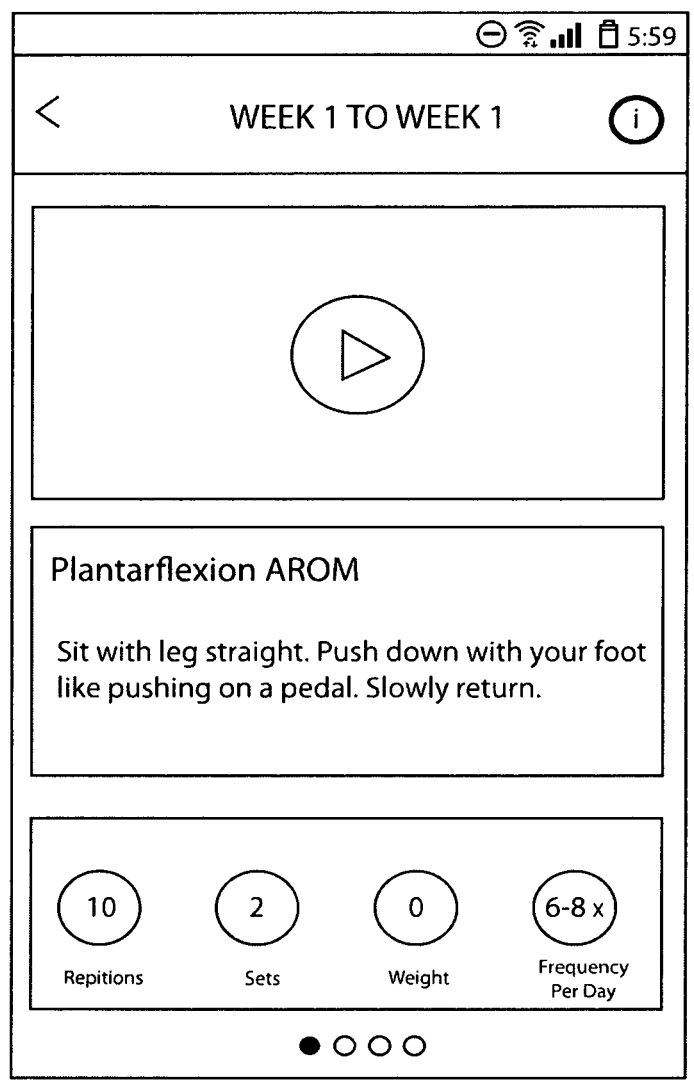
FIG. 18 shows the presentation of specific exercises for those of FIG. 17.
Figure 19:
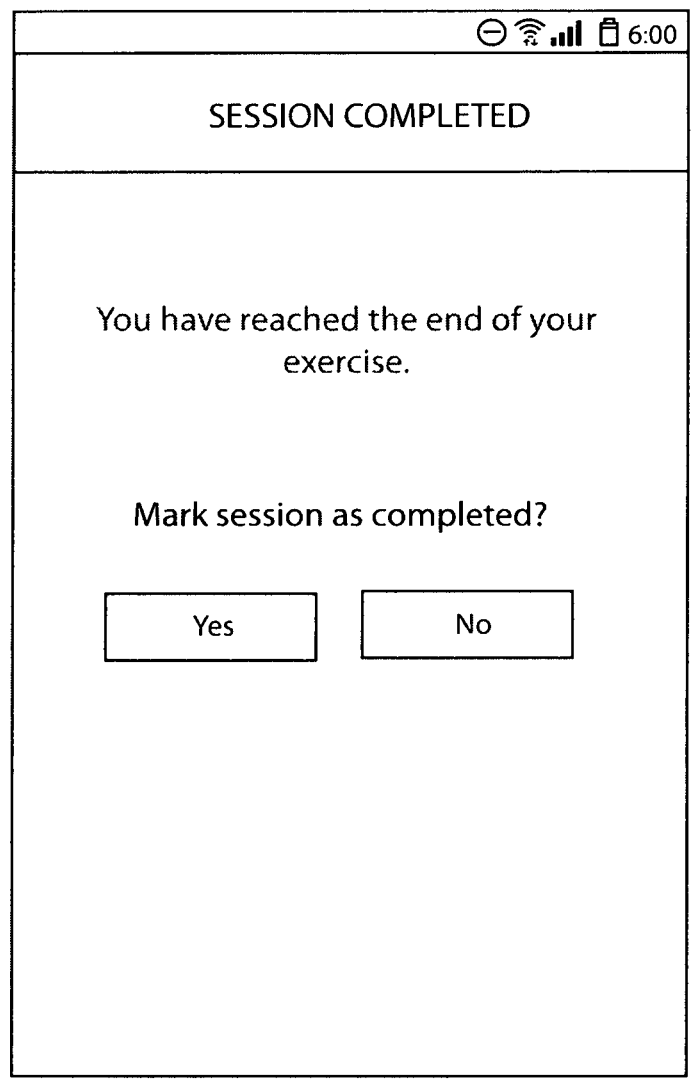
FIG. 19 provides an input for the user to indicate completion of a session.

FIG. 18 schematically shows further level of detail of the protocol, quadricep conditioning exercise routing including repetitions and frequency. A video link showing the required quadricep exercises is shown in FIG. 18, however, this could also include or be replaced by one or more images demonstrating the exercises. Once a user has completed all the necessary exercises and necessary frequency, an indication shown in FIG. 19 is provided when the session has been completed.

At predetermined times during use of the protocol, a user is required to enter their current level of pain associated with their injury, being the meniscal tear in the preferred embodiment. This can be entered before, during or after use of the protocol on each occasion, for example daily.

Figure 20:
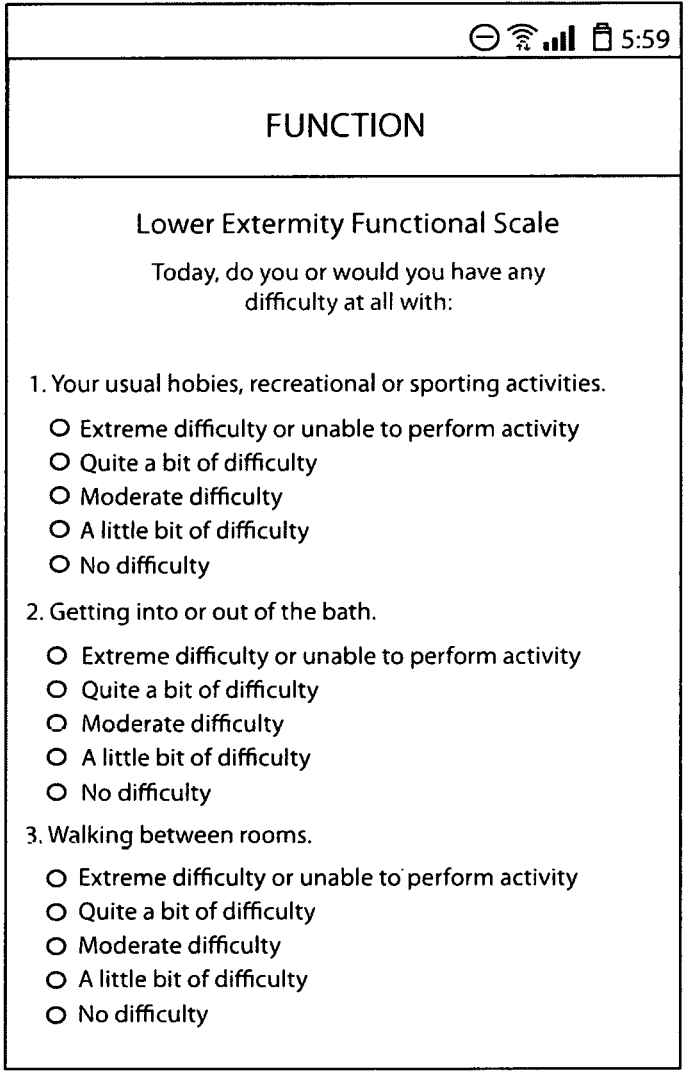
FIG. 20 is similar to FIG. 22 but for receiving a user functional score.

In FIG. 20, a lower extremity functional scale as appropriate for a meniscal tear is acquired by the user on a regular basis (weekly in the preferred embodiment), similarly to acquiring pain scores (daily). The lower extremity functional scale is used in view of the meniscal tear being the selected injury and that functional scale is described further below.

Figure 22:
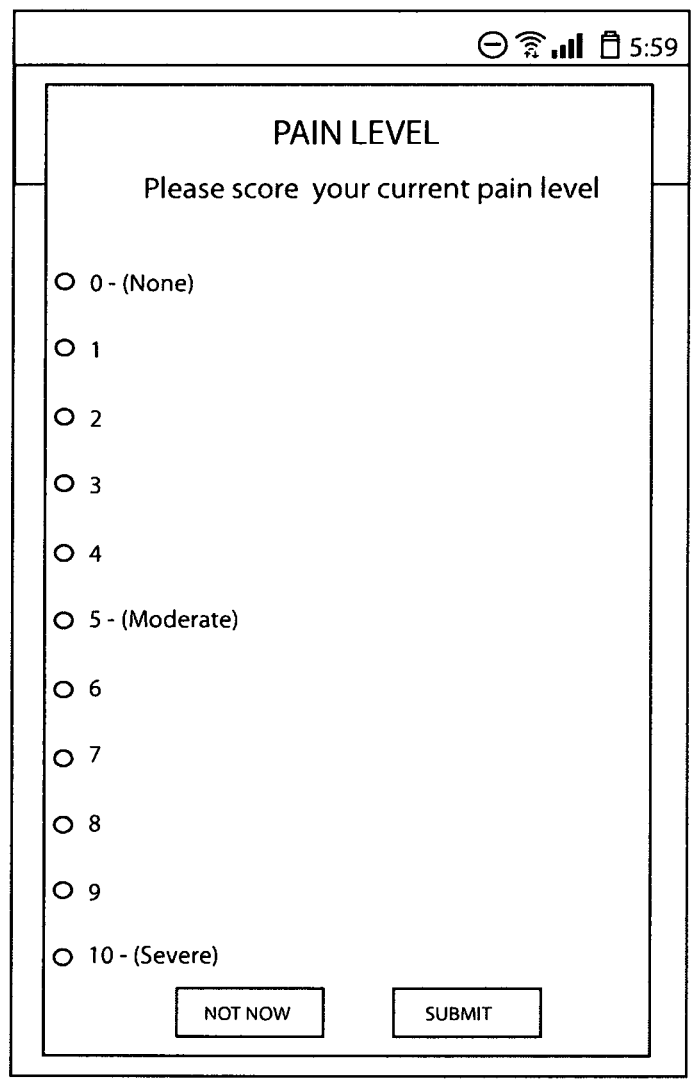
FIG. 22 shows a simulated screenshot for a user to enter a pain level.
Figure 23:
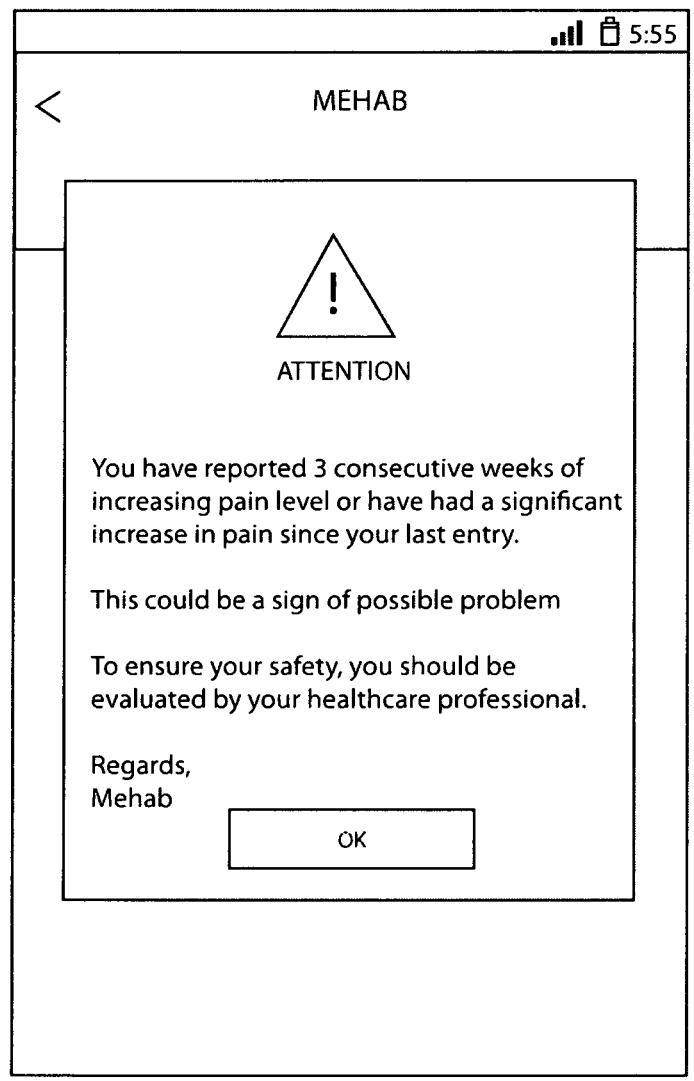
FIG. 23 is an example of an alert received by the user interrupting the protocol.

When the pain levels, nominally from 0-10, entered by the user increase for a predetermined period, three days in the preferred embodiment of FIG. 22, a warning is provided to the user indicating they should seek professional medical assistance. This most advantageously prevents a user from possibly worsening their injury or not rehabilitating it in the appropriate time frame, or if there has been exacerbation of the injury during other normal activities. FIG. 23 is a similar screenshot of information for the user if during any three weeks through the protocol continuously have decreased concerning the functional level of the user. Such may be indicative of a worse than initially considered meniscal tear or that the functional ability of the user is not progressing as would be properly expected. In the case of the pain level or the functional level warning of FIGS. 20 and 23 respectively, an option is provided for mobile or other interventional therapy and this is described further below.

In respect of the user evaluating their function level or pain level, this is done initially in response to predetermined questions set out according to the injury and the physiotherapeutic protocol selected by the user. In the case of a meniscal tear in the preferred embodiment, FIG. 24 is an example of a prior known lower extremity functional scale evaluation questionnaire. The user scores their functionality according to the results of the lower extremity functional scale. In the case of other injuries, such as a neck injury, for example, a neck disability index such as set out in FIG. 25 can be used to evaluate functional levels about injuries in those regions. Similarly, FIG. 26 shows a known questionnaire for general user functionality that could also be used. It will be appreciated that any preferred evidence based functional assessment guide can be employed for the user benefit as desired.

So far as the measure of a user's functional level can be determined in any preferred manner such as by the lower extremity functional scale shown in FIG. 24 for the meniscal tear, the user assesses their functional levels. Those functional levels are entered onto a system operating the protocol, whether locally on the smartphone device of the preferred embodiment or remote in the case of a thin-client server, for example.

It will be appreciated that the first functional level provided will correspond to a base line or initial user functionality. After a first week of physiotherapeutic protocol is completed by the user, they assess their functional level again. This is entered into the system. In the preferred embodiment shown, the functional level is measured once per week. In this case, the next functional level is determined by the user and entered accordingly. Following a subsequent period of one week, the subsequent user functional score is entered. Whilst the user is able to carry out the protocol, the method of a preferred embodiment determines if both the conditions that the second weekly functional score is not an improvement on the first and the third entered functional score also not an improvement over the second functional score entered by the user, the method includes a step of alerting the user that they have decreased functional scores that may be indicative of either ineffective treatment or the possibility of exacerbating the injury for which treatment is sought.

Figure 21:
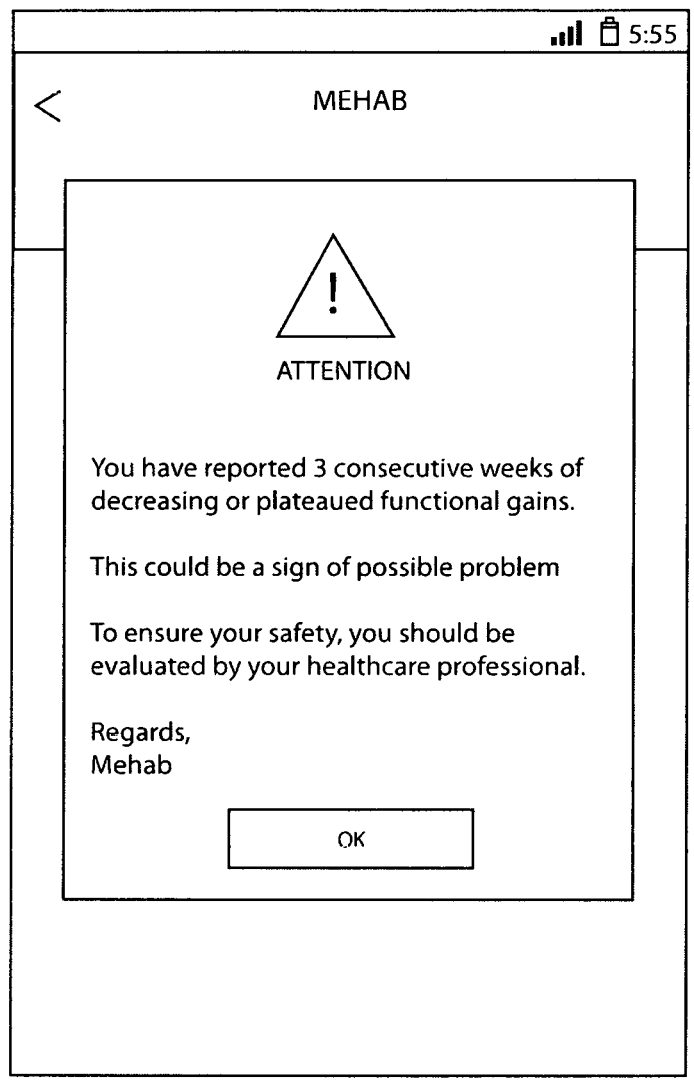
FIG. 21 is similar to FIG. 23.

This is shown in FIG. 21 as interrupting and intervening the protocol to alert the user. If there is only a drop in user functional score between one week or the next but not the week immediately either side, no alert is provided. This advantageously alerts the user that the physiotherapeutic protocol may not be providing the benefit it is expected or may be exacerbating the user's injury. As shown in FIG. 21, the user can seek the assistance of a medical professional or can continue the protocol should they desire. A mobile therapy tab is also selected where the user may be directed toward an appropriate health care professional that is close to their area based on registration details provided when the user commences the protocol, or the method may use geolocation of the user's computing device, smartphone in the preferred embodiment, to direct the user to a proximal medical practitioner. In an alternative preferred embodiment, not illustrated, selecting the mobile therapy option may alert a health care professional to contact the user. This is most advantageous as it removes the need for seeing a health care professional unless necessary.

Figure 27:
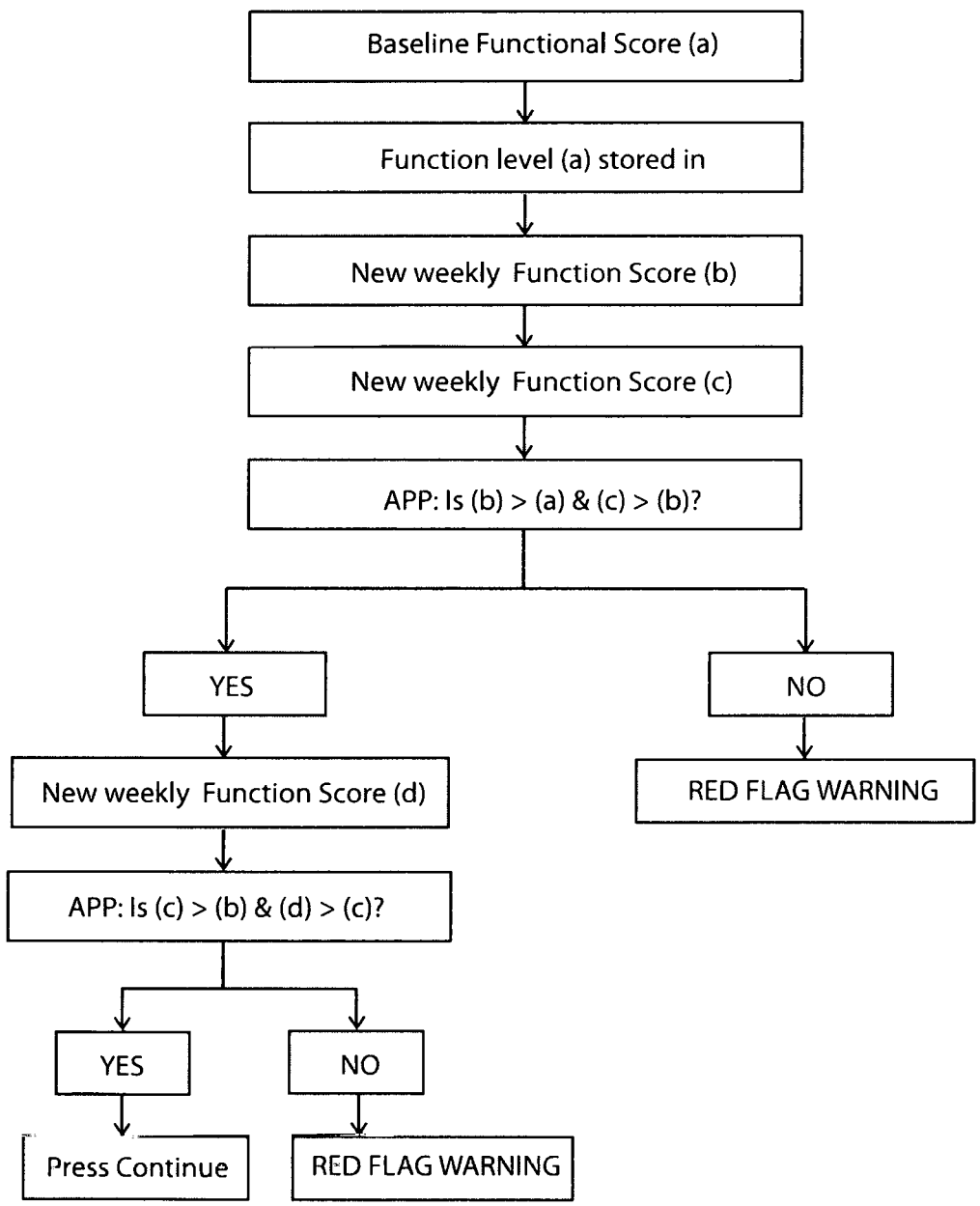
FIG. 27 is flow chart of method according to the preferred embodiment for alerting the user and interrupting the treatment protocol.

Turning to FIG. 27, there is shown the process for alerting the user and interrupting the protocol. If the functional score of the user does not decrease for two weeks in a row, they progress so that the next week in the protocol, that week and the two proceeding weeks are compared for functional levels. If there is a decrease or plateau for two continuous weeks, the protocol is interrupted and the user is alerted. Likewise, if the functional level of the user drops significantly from any previous entry, the user is also alerted and the protocol interrupted.

Although the meniscal tear physiotherapeutic protocol shown in FIG. 16 is set out in two week blocks, the user's pain level is determined on a daily basis. An initial user pain level is determined and this can similarly be consistently achieved by a user responding to a predetermined questionnaire concerning pain levels as would be associated with an injury such as a selected to the protocol, such as the meniscal tear in the present case.

Figure 28:
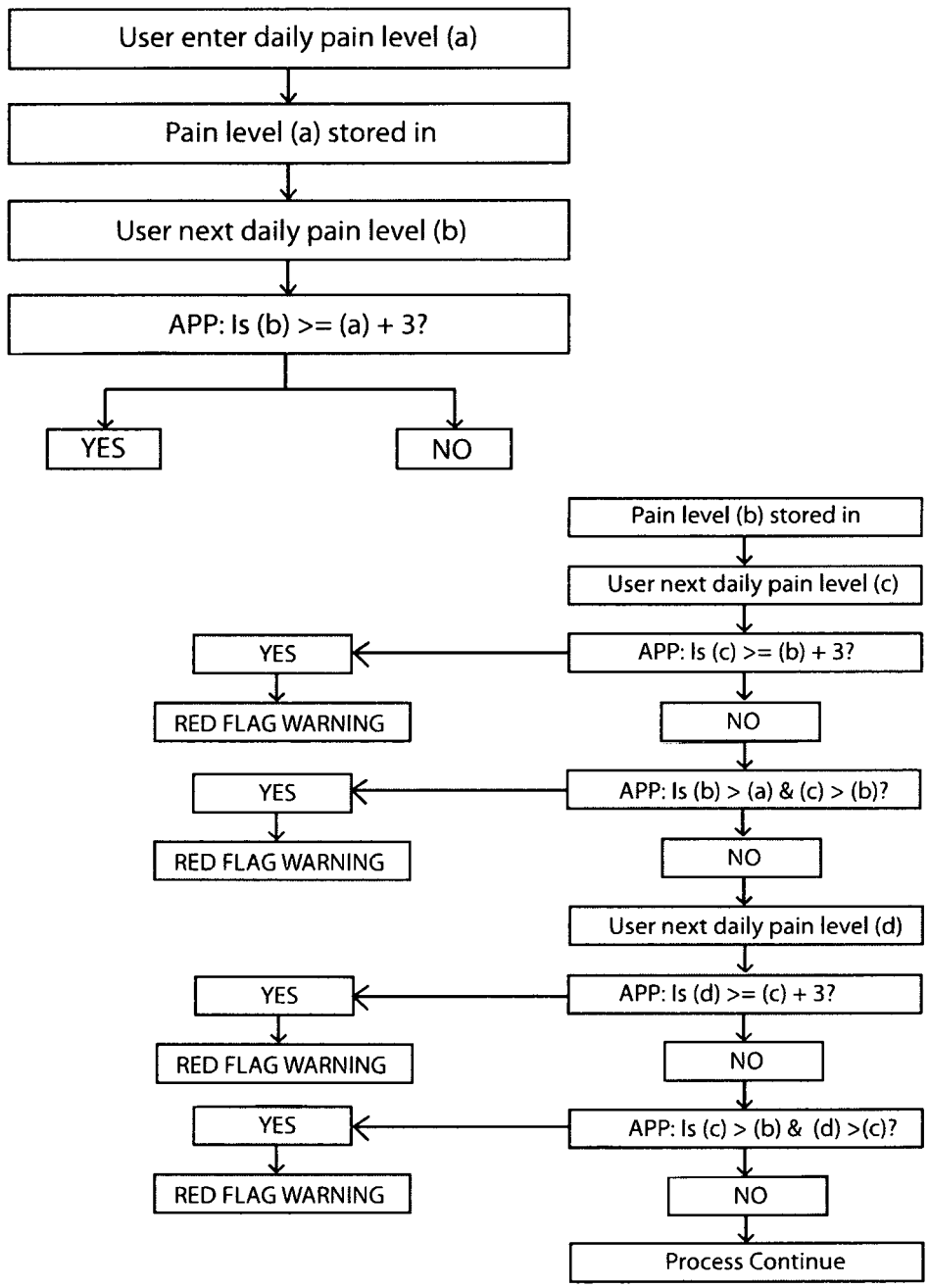
FIG. 28 is a flow chart of pain level entries for the user and for providing an alert to interrupt the treatment protocol.

In FIG. 28, a flow chart representation of the provision of an alert and interrupting the protocol for the user should their pain levels worsen either consistently or dramatically. In the flow chart of FIG. 28, the user enters a first daily pain level (a) this is stored and subsequent day the user enters their next pain level (b) using the same method of determination. If the second pain level is greater than the first pain level plus some arbitrary factor of three in the preferred embodiment, the user is alerted that they should seek professional care and the protocol discontinued. If the second pain level is not greater than the first pain level plus a factor of three, the user continues. On the third day the user provides a third daily pain level (c) and this is compared to the second pain level (b). If the third pain level is greater than or equal to the second pain level plus an arbitrary factor of three, the user is alerted and the protocol stopped. If not, both the second user pain level (b) is compared to pain level (a) and if the second is greater than the first and the third is greater than the second an alert is again sent to the user and the protocol interrupted.

If not, the user enters a fourth daily pain level (d). If this is greater than the third daily pain level (c) plus the factor of three, the user is alerted and the protocol is stopped. Such an alert is shown in FIG. 23. If the pain level has not increased by the amount of three over the third pain level (c), the third pain level is compared to the second and if greater together with the fourth pain level (d) being greater than the third pain level, the user is alerted and the protocol interrupted. In other circumstances, the process is continued.

In this way, it will be appreciated that using objective functional or pain scores can allow a user to receive or to participate in a physiotherapeutic protocol for treating an injury without necessarily having to visit a health care professional. This is not left to the user and the alerts are provided to ensure treatment is having some predetermined physiotherapeutic value and also any injury is not exacerbated or further injured by conducting the protocol.

The foregoing describes only one embodiment of the present invention and modifications, obvious to those skilled in the art, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. A method of providing a physiotherapeutic treatment protocol to a user having an injury, the method comprising the steps of:
   providing access to the user to download or install a predetermined computing application;
   registering details of the user of the installed computing application;
   determining a physiotherapeutic treatment protocol for the user in response to user selection of one or more predetermined injuries, the physiotherapeutic treatment protocol including a plurality of sessions of physiotherapeutic treatment exercises and techniques;
   receiving predetermined information from the user corresponding to functional levels of the user about their injury or damaged site and establishing one or more initial user functional levels;
   guiding the user through the physiotherapeutic treatment protocol exercises and techniques in a predetermined order;
   receiving before and/or during and/or after each treatment session user functional levels;
   wherein for three successive user functional level entries I, II and III alerting the user and interrupting the physiotherapeutic treatment protocol if functional levels I compared to II, and II compared to III exceed predetermined values, or if there is no improvement in functional level between functional levels I and II and levels II and III.

2. A method according to claim 1 wherein, pain levels or function levels entered by the user are entered daily.

3. A method according to claim 1 including the step of providing to the user physiotherapeutic treatment protocol timeframes, the physiotherapeutic treatment protocol timeframes indicative of expected healing times; and/or incremental exercise progression and/or transitions to one or more subsequent phases of exercise.

4. A method according to claim 1 including the steps of providing one or more objective measures for the user to characterise their injury, the objective measures being selected corresponding to the nature and location of the injury.

5. A method according to claim 1 wherein the step of alerting the user includes communicating with the user via a message to user computer or smartphone, and/or alerting a predefined medical practitioner or one selected proximal to the user to contact that user.

6. A method of providing a physiotherapeutic treatment protocol to a user having an injury, the method comprising the steps of:
   providing access to the user to download or install predetermined computing application;
   registering details of the user of the installed computing application;
   determining a physiotherapeutic treatment protocol for the user in response to user selection of one or more predetermined injuries, the physiotherapeutic treatment protocol including a plurality of sessions of physiotherapeutic treatment exercises and techniques;
   receiving predetermined information from the user corresponding to pain levels experienced by the user about their injury or damaged site and establishing one or more initial user pain levels;
   guiding the user through the physiotherapeutic treatment protocol exercises and techniques in a predetermined order;
   receiving before and/or during and/or after each treatment session user pain levels wherein for three successive user pain level entries I, II and III alerting the user and interrupting the physiotherapeutic treatment protocol if pain levels I compared to II, and II compared to III exceed predetermined values, or if there is no improvement in pain level between functional levels I and II and levels II and III.

7. A method according to claim 6 wherein, pain levels or function levels entered by the user are entered daily.

8. A method according to claim 6 including the step of providing to the user physiotherapeutic treatment protocol timeframes, the physiotherapeutic treatment protocol timeframes indicative of expected healing times; and/or incremental exercise progression and/or transitions to one or more subsequent phases of exercise.

9. A method according to claim 6 including the steps of providing one or more objective measures for the user to characterise their injury, the objective measures being selected corresponding to the nature and location of the injury.

10. A method according to claim 6 wherein the step of alerting the user includes communicating with the user via a message to user computer or smartphone, and/or alerting a predefined medical practitioner or one selected proximal to the user to contact that user.

* * * * *